US012110316B2

(12) United States Patent
Wells

(10) Patent No.: US 12,110,316 B2
(45) Date of Patent: Oct. 8, 2024

(54) CLEAVABLE ACTIVATORS OF CXCR3 AND METHODS OF USE

(71) Applicant: University of Pittsburgh—Of the Commonwealth System of Higher Education, Pittsburgh, PA (US)

(72) Inventor: Alan H. Wells, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 522 days.

(21) Appl. No.: 17/287,480

(22) PCT Filed: Oct. 18, 2019

(86) PCT No.: PCT/US2019/056955
§ 371 (c)(1),
(2) Date: Apr. 21, 2021

(87) PCT Pub. No.: WO2020/086400
PCT Pub. Date: Apr. 30, 2020

(65) Prior Publication Data
US 2021/0388048 A1 Dec. 16, 2021

Related U.S. Application Data

(60) Provisional application No. 62/748,711, filed on Oct. 22, 2018.

(51) Int. Cl.
*C07K 14/52* (2006.01)
*C12N 9/64* (2006.01)
*A61K 38/00* (2006.01)

(52) U.S. Cl.
CPC .......... *C07K 14/522* (2013.01); *C12N 9/6491* (2013.01); *A61K 38/00* (2013.01)

(58) Field of Classification Search
CPC .............. C07K 14/522; C07K 2319/50; C07K 14/521; C12N 9/6491
See application file for complete search history.

(56) References Cited

U.S. PATENT DOCUMENTS

| | | | |
|---|---|---|---|
| 5,994,292 | A | 11/1999 | Tosato et al. |
| 8,734,775 | B2 | 5/2014 | Yates-Binder et al. |
| 9,180,167 | B2 | 11/2015 | Wells et al. |
| 9,895,419 | B2 | 2/2018 | Yates-Binder et al. |
| 2007/0116669 | A1 | 5/2007 | Merzouk et al. |
| 2016/0058852 | A1 | 3/2016 | Ter Meulen et al. |
| 2017/0000852 | A1* | 1/2017 | Yates-Binder .......... A61P 27/02 |
| 2017/0253866 | A1* | 9/2017 | Blake ....................... C12N 9/92 |

FOREIGN PATENT DOCUMENTS

| | | |
|---|---|---|
| CA | 3039316 | 5/2018 |
| GB | 2 377 444 | 1/2003 |
| JP | 2003-526315 | 9/2003 |
| WO | WO 99/20759 | 4/1999 |
| WO | WO 2013/032853 | 3/2013 |
| WO | WO 2018/191438 | 10/2018 |

OTHER PUBLICATIONS

Bolitho et al (The chemokine CXCL1 induces proliferation in epithelial ovarian cancer cells by transactivation of the epidermal growth factor receptor. Endocrine-Related Cancer, vol. 17, 2010) (Year: 2017).*
Song et al (PLoS One 7(11):e50300, 2012; cited in IDS dated Apr. 21, 2021) (Year: 2012).*
BLAST comparison: human and mouse CXCL10 (Year: 2023).*
PROSPER human CXCL10 variant cleavage result (Year: 2023).*
PROSPER mouse CXCL10 variant cleavage result (Year: 2023).*
Pepscan (Year: 2015).*
CXCL10 and CXCL4 Acetylation sites (Year: 2023).*
Nomiyama et al (The evolution of mammalian chemokine genes. Cytokine and Growth Factor Reviews, vol. 21, 2010; herein after Nomiyama 2010) (Year: 2010).*
Nomiyama et al (Systematic classification of vertebrate chemokines based on conserved synteny and evolutionary history. Genes to Cells, 2013; cited in IDS dated Sep. 20, 2023; hereinafter Nomiyama 2013) (Year: 2013).*
Denney et al (Cleavage of chemokines CCL2 and CXCL10 by matrix metalloproteinases-2 and -9: Implications for chemotaxis. Biochemical and Biophysical Research Communications 382 (2009) 341-347; cited in IDS dated Aug. 9, 2022) (Year: 2009).*
Casrouge et al., "Discrimination of agonist and antagonist forms of CXCL10 in biological samples," *Clin Exp Immunol* 167(1):137-148, 2012.
Denney et al., "Cleavage of chemokines CCL2 and CXCL10 by matrix metalloproteinases-2 and -9: Implications for chemotaxis," *Biochem Biophys Res Commun* 382(2):341-347, 2009.
Elkington et al., "The paradox of matrix metalloproteinases in infectious diseases," *Clin Exp Immunol* 142:12-20, 2005.
Howard and Galligan, "An Expanding Appreciation of the Role Chemokine Receptors Play in Cancer Progression," *Curr Pharm Des* 10(19):2377-2389, 2004.
Lorat-Jacob, "The molecular basis and functional implications of chemokine interactions with heparan sulphate," *Curr Opin Struct Biol* 19(5):543-548, 2009.
Riva et al., "Truncated CXCL10 Is Associated with Failure to Achieve Spontaneous Clearance of Acute Hepatitis C Infection," *Hepatology* 60:487-496, 2014.

(Continued)

*Primary Examiner* — Valarie E Bertoglio
*Assistant Examiner* — Matasha Dhar
(74) *Attorney, Agent, or Firm* — Klarquist Sparkman, LLP

(57) ABSTRACT

Recombinant C-X-C motif chemokine ligand (CXCL) peptides modified to introduce a cleavage site for a protease, such as a protease activated during an inflammatory response, are described. The CXCL peptides have the capacity to activate CXCR3 until being cleaved by the protease. Proteolytic cleavage of the CXCL peptide minimizes the pro-inflammatory response and inhibits the development of fibrosis.

9 Claims, 2 Drawing Sheets

Specification includes a Sequence Listing.

(56) References Cited

OTHER PUBLICATIONS

Zabel et al., "Chemoattractants, extracellular proteases, and the integrated host defense response," *Exp Hematol* 34(8):1021-1032, 2006.
Burster et al., "Design of Protease-resistant Myelin Basic Protein-Derived Peptides by Cleavage Site Directed Amino Acid Substitutions," *Biochem Pharmacol* 74:1514-1523, 2007.
Song et al., "PROSPER: An Integrated Feature-Based Tool for Predicting Protease Substrate Cleavage Sites," *PLoS ONE* 7(11):e50300, 2012.
International Search Report and Written Opinion for PCT/US2019/056955, mailed Mar. 11, 2020 (16 pages).
Keane et al., "IFN-γ-Inducible Protein-10 Attenuates Bleomycin-Induced Pulmonary Fibrosis Via Inhibition of Angiogenesis," *J Immunol* 163(10):5686-5692, 1999.
Tager et al., "Inhibition of Pulmonary Fibrosis by the Chemokine IP-10/CXCL10," *Am J Respir Cell Mol Biol* 31(4):395-404, 2004.
Van den Steen et al., "Carboxyterminal cleavage of the chemokines MIG and IP-10 by gelatinase B and neutrophil collagenase," *Biochem Biophys Res Commun* 310(3):889-896, 2003.
Nomiyama et al., "Systematic classification of vertebrate chemokines based on conserved synteny and evolutionary history," *Genes to Cells*, vol. 18:1-16, 2013.

* cited by examiner

SEQUENCE LISTING

<160> NUMBER OF SEQ ID NOS: 36

<210> SEQ ID NO 1
<211> LENGTH: 22
<212> TYPE: PRT
<213> ORGANISM: Homo sapiens

<400> SEQUENCE: 1

Pro Glu Ser Lys Ala Ile Lys Asn Leu Leu Lys Ala Val Ser Lys Glu
1 5 10 15

Arg Ser Lys Arg Ser Pro
20

<210> SEQ ID NO 2
<211> LENGTH: 22
<212> TYPE: PRT
<213> ORGANISM: Artificial Sequence
<220> FEATURE:

<223> OTHER INFORMATION: Synthetic peptide

<400> SEQUENCE: 2

```
Pro Glu Ser Lys Ala Ile Lys Asn Leu Leu Lys Ala Val His Lys Glu
1               5                   10                  15

Met Ser Lys Arg Ser Pro
            20
```

<210> SEQ ID NO 3
<211> LENGTH: 21
<212> TYPE: PRT
<213> ORGANISM: Artificial Sequence
<220> FEATURE:
<223> OTHER INFORMATION: Synthetic peptide

<400> SEQUENCE: 3

```
Glu Ser Lys Ala Ile Lys Asn Leu Leu Lys Ala Val His Lys Glu Met
1               5                   10                  15

Ser Lys Arg Ser Pro
            20
```

<210> SEQ ID NO 4
<211> LENGTH: 22
<212> TYPE: PRT
<213> ORGANISM: Artificial Sequence
<220> FEATURE:
<223> OTHER INFORMATION: Synthetic peptide

<400> SEQUENCE: 4

```
Pro Glu Ser Lys Ala Ile Lys Asn Leu Leu Lys Ala Val His Lys Glu
1               5                   10                  15

Arg Ser Lys Arg Ser Pro
            20
```

<210> SEQ ID NO 5
<211> LENGTH: 21
<212> TYPE: PRT
<213> ORGANISM: Artificial Sequence
<220> FEATURE:
<223> OTHER INFORMATION: Synthetic peptide

<400> SEQUENCE: 5

```
Glu Ser Lys Ala Ile Lys Asn Leu Leu Lys Ala Val His Lys Glu Arg
1               5                   10                  15

Ser Lys Arg Ser Pro
            20
```

<210> SEQ ID NO 6
<211> LENGTH: 22
<212> TYPE: PRT
<213> ORGANISM: Artificial Sequence
<220> FEATURE:
<223> OTHER INFORMATION: Synthetic peptide

<400> SEQUENCE: 6

```
Pro Glu Ser Lys Ala Ile Lys Asn Leu Leu Lys Ala Val Ser Glu Val
1               5                   10                  15

Leu Ser Lys Arg Ser Pro
            20
```

<210> SEQ ID NO 7
<211> LENGTH: 22
<212> TYPE: PRT
<213> ORGANISM: Artificial Sequence
<220> FEATURE:
<223> OTHER INFORMATION: Synthetic peptide

<400> SEQUENCE: 7

```
Pro Glu Ser Phe Ile Arg Trp Asn Leu Leu Lys Ala Val Ser Lys Glu
1               5                   10                  15

Met Ser Lys Arg Ser Pro
            20
```

<210> SEQ ID NO 8
<211> LENGTH: 98
<212> TYPE: PRT
<213> ORGANISM: Homo sapiens

<400> SEQUENCE: 8

```
Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro
```

<210> SEQ ID NO 9
<211> LENGTH: 101
<212> TYPE: PRT
<213> ORGANISM: Homo sapiens

<400> SEQUENCE: 9

```
Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala Glu
            20                  25                  30

Ala Glu Glu Asp Gly Asp Leu Gln Cys Leu Cys Val Lys Thr Thr Ser
        35                  40                  45

Gln Val Arg Pro Arg His Ile Thr Ser Leu Glu Val Ile Lys Ala Gly
    50                  55                  60

Pro His Cys Pro Thr Ala Gln Leu Ile Ala Thr Leu Lys Asn Gly Arg
65                  70                  75                  80

Lys Ile Cys Leu Asp Leu Gln Ala Pro Leu Tyr Lys Lys Ile Ile Lys
                85                  90                  95

Lys Leu Leu Glu Ser
            100
```

<210> SEQ ID NO 10
<211> LENGTH: 125
<212> TYPE: PRT
<213> ORGANISM: Homo sapiens

<400> SEQUENCE: 10

```
Met Lys Lys Ser Gly Val Leu Phe Leu Leu Gly Ile Ile Leu Leu Val
1               5                   10                  15
```

```
Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
    50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Lys Val Leu Lys
            100                 105                 110

Val Arg Lys Ser Gln Arg Ser Arg Gln Lys Lys Thr Thr
        115                 120                 125


<210> SEQ ID NO 11
<211> LENGTH: 94
<212> TYPE: PRT
<213> ORGANISM: Homo sapiens

<400> SEQUENCE: 11

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90


<210> SEQ ID NO 12
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = Leu, His or Phe
<220> FEATURE:
<221> NAME/KEY: MISC_FEATURE
<222> LOCATION: (6)..(6)
<223> OTHER INFORMATION: Xaa = Ser or no amino acid

<400> SEQUENCE: 12

Xaa Val Leu Xaa Ser Xaa Ala Val
1               5


<210> SEQ ID NO 13
<211> LENGTH: 4
<212> TYPE: PRT
<213> ORGANISM: Artificial Sequence
<220> FEATURE:
<223> OTHER INFORMATION: Synthetic peptide
```

<400> SEQUENCE: 13

Phe Ile Arg Trp
1

<210> SEQ ID NO 14
<211> LENGTH: 29
<212> TYPE: PRT
<213> ORGANISM: Homo sapiens

<400> SEQUENCE: 14

Asp Leu Gln Cys Leu Cys Val Lys Thr Thr Ser Gln Val Arg Pro Arg
1 5 10 15

His Ile Thr Ser Leu Glu Val Ile Lys Ala Gly Pro His
20 25

<210> SEQ ID NO 15
<211> LENGTH: 13
<212> TYPE: PRT
<213> ORGANISM: Homo sapiens

<400> SEQUENCE: 15

Pro Leu Tyr Lys Lys Ile Ile Lys Lys Leu Leu Glu Ser
1 5 10

<210> SEQ ID NO 16
<211> LENGTH: 18
<212> TYPE: PRT
<213> ORGANISM: Homo sapiens

<400> SEQUENCE: 16

Leu Asp Leu Gln Ala Pro Leu Tyr Lys Lys Ile Ile Lys Lys Leu Leu
1 5 10 15

Glu Ser

<210> SEQ ID NO 17
<211> LENGTH: 29
<212> TYPE: PRT
<213> ORGANISM: Artificial Sequence
<220> FEATURE:
<223> OTHER INFORMATION: Synthetic peptide

<400> SEQUENCE: 17

Asp Leu Gln Cys Leu Cys Val Lys Thr Thr Ser Gln Val Arg Pro Arg
1 5 10 15

His Ile Thr Ser Leu Glu Gly Ile Lys Ala Gly Pro His
20 25

<210> SEQ ID NO 18
<211> LENGTH: 29
<212> TYPE: PRT
<213> ORGANISM: Artificial Sequence
<220> FEATURE:
<223> OTHER INFORMATION: Synthetic peptide

<400> SEQUENCE: 18

Asp Leu Gln Cys Leu Cys Val Lys Thr Thr Ser Gln Val Arg Pro Arg
1 5 10 15

His Ile Thr Ser Leu Glu Glu Ile Lys Ala Gly Pro His
20 25

<210> SEQ ID NO 19
<211> LENGTH: 13

<212> TYPE: PRT
<213> ORGANISM: Artificial Sequence
<220> FEATURE:
<223> OTHER INFORMATION: Synthetic peptide

<400> SEQUENCE: 19

```
Pro Leu Tyr Lys Lys Ile Ile Lys Lys Leu Glu Glu Ser
1               5                   10
```

<210> SEQ ID NO 20
<211> LENGTH: 18
<212> TYPE: PRT
<213> ORGANISM: Artificial Sequence
<220> FEATURE:
<223> OTHER INFORMATION: Synthetic peptide

<400> SEQUENCE: 20

```
Leu Asp Leu Gln Ala Pro Leu Tyr Lys Lys Ile Ile Lys Lys Leu Glu
1               5                   10                  15

Glu Ser
```

<210> SEQ ID NO 21
<211> LENGTH: 29
<212> TYPE: PRT
<213> ORGANISM: Artificial Sequence
<220> FEATURE:
<223> OTHER INFORMATION: Synthetic peptide

<400> SEQUENCE: 21

```
Asp Leu Gln Cys Leu Cys Val Lys Thr Thr Ser Gln Val Arg Pro Arg
1               5                   10                  15

Leu Ile Thr Ser Leu Glu Val Ile Lys Ala Gly Pro His
            20                  25
```

<210> SEQ ID NO 22
<211> LENGTH: 13
<212> TYPE: PRT
<213> ORGANISM: Artificial Sequence
<220> FEATURE:
<223> OTHER INFORMATION: Synthetic peptide

<400> SEQUENCE: 22

```
Pro Leu Tyr Pro Lys Ile Ile Lys Lys Leu Leu Glu Ser
1               5                   10
```

<210> SEQ ID NO 23
<211> LENGTH: 18
<212> TYPE: PRT
<213> ORGANISM: Artificial Sequence
<220> FEATURE:
<223> OTHER INFORMATION: Synthetic peptide

<400> SEQUENCE: 23

```
Leu Asp Leu Gln Ala Pro Leu Tyr Pro Lys Ile Ile Lys Lys Leu Leu
1               5                   10                  15

Glu Ser
```

<210> SEQ ID NO 24
<211> LENGTH: 18
<212> TYPE: PRT
<213> ORGANISM: Homo sapiens

<400> SEQUENCE: 24

```
Pro Lys Ser Lys Gln Ala Arg Leu Ile Ile Lys Lys Val Glu Arg Lys
1               5                   10                  15
```

Asn Phe

<210> SEQ ID NO 25
<211> LENGTH: 20
<212> TYPE: PRT
<213> ORGANISM: Homo sapiens

<400> SEQUENCE: 25

Leu Asn Pro Lys Ser Lys Gln Ala Arg Leu Ile Ile Lys Lys Val Glu
1 5 10 15

Arg Lys Asn Phe
20

<210> SEQ ID NO 26
<211> LENGTH: 16
<212> TYPE: PRT
<213> ORGANISM: Homo sapiens

<400> SEQUENCE: 26

Asp Lys Ile Glu Val Ile Ile Thr Leu Lys Glu Asn Lys Gly Gln Arg
1 5 10 15

<210> SEQ ID NO 27
<211> LENGTH: 18
<212> TYPE: PRT
<213> ORGANISM: Artificial Sequence
<220> FEATURE:
<223> OTHER INFORMATION: Synthetic peptide

<400> SEQUENCE: 27

Pro Lys Ser Lys Gln Ala Arg Leu Ile Ile Lys Lys Val Glu Glu Lys
1 5 10 15

Asn Phe

<210> SEQ ID NO 28
<211> LENGTH: 18
<212> TYPE: PRT
<213> ORGANISM: Artificial Sequence
<220> FEATURE:
<223> OTHER INFORMATION: Synthetic peptide

<400> SEQUENCE: 28

Pro Lys Ser Lys Gln Ala Arg Leu Ile Ile Lys Lys Val Glu Gly Lys
1 5 10 15

Asn Phe

<210> SEQ ID NO 29
<211> LENGTH: 20
<212> TYPE: PRT
<213> ORGANISM: Artificial Sequence
<220> FEATURE:
<223> OTHER INFORMATION: Synthetic peptide

<400> SEQUENCE: 29

Leu Asn Pro Lys Ser Lys Gln Ala Arg Leu Ile Ile Lys Lys Val Glu
1 5 10 15

Glu Lys Asn Phe
20

<210> SEQ ID NO 30
<211> LENGTH: 20
<212> TYPE: PRT
<213> ORGANISM: Artificial Sequence
<220> FEATURE:
<223> OTHER INFORMATION: Synthetic peptide

<400> SEQUENCE: 30

```
Leu Asn Pro Lys Ser Lys Gln Ala Arg Leu Ile Ile Lys Lys Val Glu
1               5                   10                  15

Gly Lys Asn Phe
            20
```

<210> SEQ ID NO 31
<211> LENGTH: 16
<212> TYPE: PRT
<213> ORGANISM: Artificial Sequence
<220> FEATURE:
<223> OTHER INFORMATION: Synthetic peptide

<400> SEQUENCE: 31

```
Asp Lys Ile Glu Val Ile Ile Thr Leu Glu Glu Asn Lys Gly Gln Arg
1               5                   10                  15
```

<210> SEQ ID NO 32
<211> LENGTH: 18
<212> TYPE: PRT
<213> ORGANISM: Artificial Sequence
<220> FEATURE:
<223> OTHER INFORMATION: Synthetic peptide

<400> SEQUENCE: 32

```
Pro Lys Ser Lys Pro Ala Arg Leu Ile Ile Lys Lys Val Glu Arg Lys
1               5                   10                  15

Asn Phe
```

<210> SEQ ID NO 33
<211> LENGTH: 20
<212> TYPE: PRT
<213> ORGANISM: Artificial Sequence
<220> FEATURE:
<223> OTHER INFORMATION: Synthetic peptide

<400> SEQUENCE: 33

```
Leu Asn Pro Lys Ser Lys Pro Ala Arg Leu Ile Ile Lys Lys Val Glu
1               5                   10                  15

Arg Lys Asn Phe
            20
```

<210> SEQ ID NO 34
<211> LENGTH: 16
<212> TYPE: PRT
<213> ORGANISM: Artificial Sequence
<220> FEATURE:
<223> OTHER INFORMATION: Synthetic peptide

<400> SEQUENCE: 34

```
Asp Lys Pro Glu Val Ile Ile Thr Leu Lys Glu Asn Lys Gly Gln Arg
1               5                   10                  15
```

<210> SEQ ID NO 35
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid

```
<220> FEATURE:
<221> NAME/KEY: MISC_FEATURE
<222> LOCATION: (3)..(3)
<223> OTHER INFORMATION: Xaa = Leu, Pro or Val
<220> FEATURE:
<221> NAME/KEY: MISC_FEATURE
<222> LOCATION: (4)..(4)
<223> OTHER INFORMATION: Xaa = Glu or Ala
<220> FEATURE:
<221> NAME/KEY: MISC_FEATURE
<222> LOCATION: (5)..(5)
<223> OTHER INFORMATION: Xaa = Gly or Glu
<220> FEATURE:
<221> NAME/KEY: misc_feature
<222> LOCATION: (6)..(8)
<223> OTHER INFORMATION: Xaa can be any naturally occurring amino acid

<400> SEQUENCE: 35

Xaa Xaa Xaa Xaa Xaa Xaa Xaa Xaa
1               5


<210> SEQ ID NO 36
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa = Leu or Ile
<220> FEATURE:
<221> NAME/KEY: misc_feature
<222> LOCATION: (6)..(8)
<223> OTHER INFORMATION: Xaa can be any naturally occurring amino acid

<400> SEQUENCE: 36

Xaa Pro Xaa Xaa Xaa Xaa Xaa Xaa
1               5
```

CLEAVABLE ACTIVATORS OF CXCR3 AND METHODS OF USE

CROSS REFERENCE TO RELATED APPLICATIONS

This application is the U.S. National Stage of International Application No. PCT/US2019/056955, filed Oct. 18, 2019, published in English under PCT Article 21(2), which claims the benefit of U.S. Application No. 62/748,711, filed Oct. 22, 2018, which is herein incorporated by reference in its entirety.

FIELD

This disclosure concerns peptide activators of C-X-C chemokine receptor 3 (CXCR3) that can be cleaved by proteases present at sites of inflammation, and methods of their use, such as for inhibiting fibrosis without causing inflammation.

BACKGROUND

The chemokine receptor CXCR3 is a G-protein coupled receptor in the C-X-C chemokine receptor family CXCR3 is primarily expressed on activated T lymphocytes and natural killer (NK) cells. Ligands for CXCR3 include C-X-C motif chemokine ligand 4 (CXCL4), CXCL9, CXCL10 and CXCL11. Binding of these ligands to CXCR3 results in pleiotropic effects, including anti-fibrotic effects on adherent cells, and pro-inflammatory and fibrotic effects on cells of the innate immune system. Activators of CXCR3 can limit fibrosis and angiogenesis when signaling through CXCR3 receptors expressed on fibroblast cells, endothelial cells and other adherent cells. However, activation of CXCR3 on immune cells can promote inflammatory scarring and fibrosis.

SUMMARY

Described herein are recombinant C-X-C motif chemokine ligand (CXCL) peptides that are modified to introduce a cleavage site for a protease, such as a protease activated during an inflammatory response. The disclosed peptides have the capacity to activate CXCR3 until being cleaved by the protease. Proteolytic cleavage of the CXCL peptide minimizes the pro-inflammatory response and inhibits the development of fibrosis.

Provided herein are recombinant CXCL peptides modified relative to a wild-type CXCL amino acid sequence to introduce a cleavage site for a protease. In some embodiments, the CXCL is a ligand for C-X-C chemokine receptor 3 (CXCR3), such as CXCL10, CXCL4, CXCL9 or CXCL11. In some embodiments, the protease is a cathepsin, an elastase or a matrix metalloproteinase (MMP).

Compositions that include a recombinant CXCL peptide disclosed herein are also provided. The compositions can be formulated, for example, for topical, intranasal, inhalation, intravenous, intravitreal, intramuscular, intradermal, or subcutaneous administration. In some embodiments, the composition is in unit-dose form.

Also provided are methods of inhibiting fibrosis in a subject. In some embodiments, the method includes administering to the subject a CXCL peptide or composition disclosed herein. In some examples, the subject has a wound, an autoimmune disease, an inflammatory disease or disorder, or an iatrogenic disease or disorder.

Further provided are methods of inhibiting angiogenesis in a subject. In some embodiments, the method includes administering to the subject a CXCL peptide or composition disclosed herein. In some examples, the subject has an angiogenic disorder of the eye.

The foregoing and other objects, features, and advantages of the invention will become more apparent from the following detailed description, which proceeds with reference to the accompanying FIGURES.

SEQUENCE LISTING

Figure 1A:
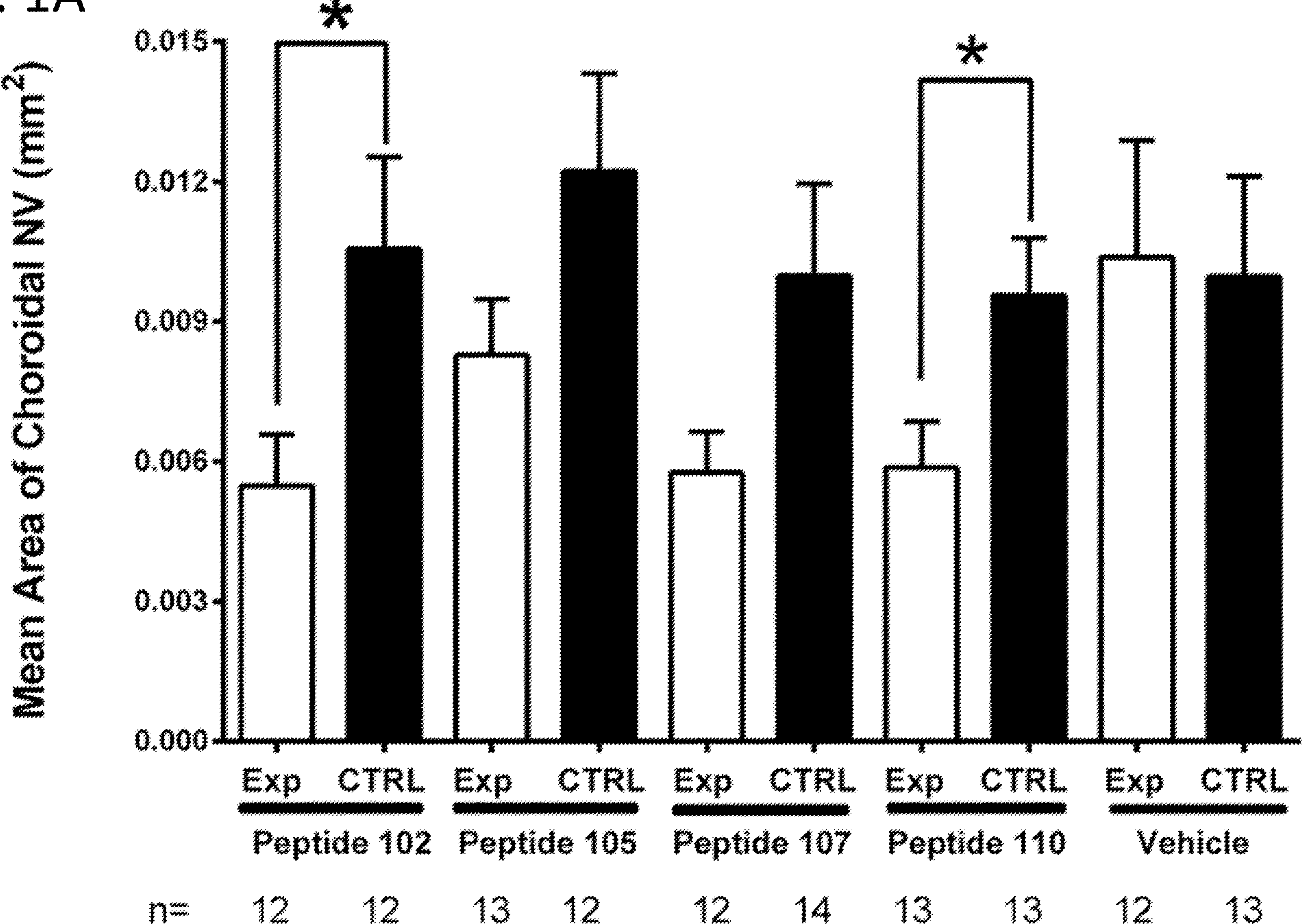
FIGS. 1A-1B: Efficacy of a CXCL10-derived cleavable peptide in blocking choroidal neovascularization (CNV). Modified Peptide 110 (SEQ ID NO: 2) was tested in a mouse model of CNV. Mice were administered vehicle, Peptide 110, a positive control peptide (Peptide 102, 105 or 107), or a corresponding scramble peptide as a control. Peptides were administered at a dose of 1 μg (FIG. 1A) or 3 μg (FIG. 1B). Exp=experimental peptide; CTRL=scramble control peptide.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Apr. 19, 2021, 13.3 KB, which is incorporated by reference herein. In the accompanying sequence listing:

SEQ ID NO: 1 is the amino acid sequence of a wild-type CXCL10 peptide.

SEQ ID NOs: 2-7 are the amino acid sequences of modified CXCL10 peptides. The C-terminal proline residue of each peptide is optionally amidated or methylated.

SEQ ID NO: 8 is the amino acid sequence of human CXCL10.

SEQ ID NO: 9 is the amino acid sequence of human CXCL4.

SEQ ID NO: 10 is the amino acid sequence of human CXCL9.

SEQ ID NO: 11 is the amino acid sequence of human CXCL11.

SEQ ID NO: 12 is the amino acid sequence of a cathepsin G recognition site.

SEQ ID NO: 13 is the amino acid sequence of a neutrophil elastase recognition site.

SEQ ID NOs: 14-16 are the amino acid sequences of wild-type CXCL4 peptides.

SEQ ID NOs: 17-23 are the amino acid sequences of modified CXCL4 peptides.

SEQ ID NOs: 24-26 are the amino acid sequences of wild-type CXCL11 peptides.

SEQ ID NOs: 27-34 are the amino acid sequences of modified CXCL11 peptides.

SEQ ID NO: 35 is the amino acid sequence of a cathepsin K recognition site.

SEQ ID NO: 36 is the amino acid sequence of a MMP2 recognition site.

DETAILED DESCRIPTION

I. Abbreviations

BCG Bacillus Calmette-Guerin

CNV choroidal neovascularization

CXCR3 C-X-C chemokine receptor 3
CXCL4 chemokine (C-X-C motif) ligand 4
CXCL9 chemokine (C-X-C motif) ligand 9
CXCL10 chemokine (C-X-C motif) ligand 10
CXCL11 chemokine (C-X-C motif) ligand 11
FITC fluorescein isothiocyanate
IP-10 interferon-y-inducible 10 kDa protein
IPF idiopathic pulmonary fibrosis
MMP matrix metalloproteinase
NV neovascularization
PLGA poly(lactic-co-glycolic acid)

II. Terms and Methods

Unless otherwise noted, technical terms are used according to conventional usage. Definitions of common terms in molecular biology may be found in Benjamin Lewin, *Genes X,* published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administration: The introduction of a composition (such as a protein or peptide) into a subject by a chosen route. For example, if the chosen route is intravenous, the composition is administered by introducing the composition into a vein of the subject. Exemplary routes of administration include, but are not limited to, injection (such as intraocular, intravitreal, subcutaneous, intramuscular, intradermal, intraperitoneal, and intravenous), oral, intraductal, sublingual, transdermal, intranasal, topical, inhalation routes and via a medical implant.

Angiogenesis: The physiological process involving the growth of new blood vessels from pre-existing vessels. Angiogenesis is a normal and vital process in growth and development, as well as in wound healing and in granulation tissue. However, it is also a fundamental step in the transition of tumors from a dormant state to a malignant one, and a number of other disorders result from aberrant angiogenesis. "Aberrant angiogenesis" refers to uncontrolled or pathologic angiogenesis present in a number of different diseases, including disorders of the eye, for example, restenosis following glaucoma treatment, wet macular degeneration, diabetic retinopathy, retinopathy of prematurity or neovascular glaucoma.

Angiogenic disorder: Any condition, disease or disorder resulting from aberrant angiogenesis. Examples of angiogenic disorders include, for example, cancer, diabetic retinopathy, macular degeneration, retinopathy of prematurity, corneal neovascularization and neovascular glaucoma. This term also includes conditions resulting from aberrant pathologic angiogenesis resulting from medical interventions, such as restenosis following glaucoma treatment and angiogenesis resulting from corneal transplant.

Angiogenic disorder of the eye: Includes any intraocular or external angiogenic disorder of the eye. For example, intraocular angiogenic disorders include disorders inside the eye such as diabetic retinopathy, wet macular degeneration, retinopathy of prematurity, restenosis following glaucoma treatment and neovascular glaucoma. External angiogenic disorders of the eye are exterior to the eye, for example corneal neovascularization.

Autoimmune disease: A disorder in which the immune system produces an immune response (e.g. a B cell or a T cell response) against an endogenous antigen, with consequent injury to tissues. Autoimmune diseases included, but are not limited to, type 1 diabetes, rheumatoid arthritis, psoriasis, multiple sclerosis, systemic lupus erythematosus (lupus), inflammatory bowel disease, Addison's disease, Graves' disease, Sjögren's syndrome, Hashimoto's thyroiditis, myasthenia gravis and celiac disease.

Carrier protein: An immunogenic protein that can be attached to another molecule, such as a peptide, small molecule, or organic compound, to promote immunogenicity of the molecule. Examples of carrier proteins include, but are not limited to, bovine serum albumin, ovalbumin, and keyhole limpet hemocyanin.

Cathepsin: A type of protease. The cathepsin family of proteases includes serine proteases (cathepsin A, cathepsin G), cysteine proteases (cathepsin B, cathepsin C, cathepsin F, cathepsin H, cathepsin K, cathepsin L1, cathepsin L2, cathepsin O, cathepsin S, cathepsin W, cathepsin Z), and aspartyl proteases (cathepsin D, cathepsin E).

Cathepsin G: A serine protease known to play a role in eliminating intracellular pathogens and breaking down tissues at sites of inflammation. Cathepsin G is stored azurophil granules found in neutrophils and other immune cells.

Coacervate: Spherical aggregates of colloidal droplets held together by hydrophobic forces. Coacervate droplets are generally about 1 to 100 μm in diameter.

Conservative variants: "Conservative" amino acid substitutions are those substitutions that do not substantially affect or decrease an activity or antigenicity of a protein or peptide. For example, a peptide disclosed herein can include at most about 1, at most about 2, at most about 3, at most about 4 or at most about 5 conservative substitutions (such as 1, 2, 3, 4, or 5 conservative substitutions, and retain biological activity, such as the ability to bind CXCR3. Specific, non-limiting examples of a conservative substitution include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |

-continued

| Original Residue | Conservative Substitutions |
|---|---|
| Thr | Ser |
| Trp | Tyr |
| Tyr | Trp; Phe |
| Val | Ile; Leu |

The term conservative variant also includes the use of a substituted amino acid in place of an unsubstituted parent amino acid. Non-conservative substitutions are those that reduce an activity or antigenicity.

Corneal neovascularization: Excessive ingrowth of blood vessels from the limbal vascular plexus into the cornea, caused by a low reception of oxygen. One of the most common causes is from wearing contact lenses, particular extended wear contact lenses. Corneal neovascularization is also a common response to injury of the eye and can also occur after corneal transplant.

Chemokine (C-X-C motif) ligand 4 (CXCL4): A small cytokine belonging to the CXC chemokine family CXCL4 is also known as platelet factor 4 (PF4). CXCL4 is a 70-amino acid protein that is released from the alpha-granules of activated platelets and binds with high affinity to heparin. Its major physiologic role appears to be neutralization of heparin-like molecules on the endothelial surface of blood vessels, thereby inhibiting local antithrombin III activity and promoting coagulation. As a strong chemoattractant for neutrophils and fibroblasts, CXCL4 is believed to play a role in inflammation and wound repair. CXCL4 is known to bind the B isoform of CXCR3 (CXCR3-B). Sequences for CXCL4 are publicly available (see, for example, GENBANK™ Gene ID 5196). An exemplary human CXCL4 sequence is set forth herein as SEQ ID NO: 9.

Chemokine (C-X-C motif) ligand 9 (CXCL9): A member of the CXC chemokine family. The CXCL9 protein is thought to be involved in T cell trafficking. CXCL9 binds to CXCR3 and is a chemoattractant for lymphocytes, but not for neutrophils. Sequences for CXCL4 are publicly available (see, for example, GENBANK™ Gene ID 4283). An exemplary human CXCL9 sequence is set forth herein as SEQ ID NO: 10.

Chemokine (C-X-C motif) ligand 10 (CXCL10): A chemokine of the CXC subfamily and a ligand for the receptor CXCR3. CXCL10 is also known as interferon-γ-inducible 10 kDa protein (IP-10). Binding of this protein to CXCR3 results in pleiotropic effects, including stimulation of monocytes, natural killer and T-cell migration, modulation of adhesion molecule expression, and inhibition of vessel formation. CXCL10 sequences are publicly available, such as through GENBANK™ (see, for example, Gene ID 3627 for human IP-10 sequences; see also GENBANK™ Accession No. P02778). An exemplary human CXCL10 sequence is set forth herein as SEQ ID NO: 8.

Chemokine (C-X-C motif) ligand 11 (CXCL11): A chemokine of the CXC subfamily and a ligand for the receptor CXCR3. The CXCL11 protein induces a chemotactic response in activated T-cells and is the dominant ligand for CXCR3. The gene encoding this protein contains 4 exons and at least three polyadenylation signals which might reflect cell-specific regulation of expression. IFN-γ is a potent inducer of transcription of this gene. Sequences for CXCL11 are publicly available (see, for example, GENBANK™ Gene ID 6373). An exemplary human CXCL11 sequence is set forth herein as SEQ ID NO: 11.

CXCR3 (C-X-C chemokine receptor 3): A G protein-coupled receptor with selectivity for four chemokines, CXCL4/ PF4 (platelet factor 4), CXCL9/ Mig (monokine induced by interferon-γ), CXCL10/ IP-10 (interferon-γ-inducible 10 kDa protein) and CXCL11/ I-TAC (interferon-inducible T cell a-chemoattractant). Binding of chemokines to this protein induces cellular responses that are involved in leukocyte trafficking, most notably integrin activation, cytoskeletal changes and chemotactic migration. Alternatively spliced transcript variants encoding different isoforms have been found for this gene. One of the isoforms (CXCR3-B) shows high affinity binding to chemokine CXCL4.

Diabetic retinopathy: A disorder in which damage to the retina occurs due to complications of diabetes mellitus. Proliferative retinopathy, which generally occurs at advanced stages of the disease, is characterized by abnormal formation of new blood vessels on the vitreous surface, extending into the vitreous cavity.

Elastase: A serine protease that breaks down elastin. Elastases include chymotrypsin-like elastases, chymotrypsin elastases, neutrophil elastases and macrophage elastases. Neutrophil elastases are capable of breaking down bacterial membrane proteins and virulence factors.

Fibrosis: A condition associated with the thickening and scarring of connective tissue. Often, fibrosis occurs in response to an injury, such as from a disease or condition that damages tissue. Fibrosis is an exaggerated wound healing response that when severe, can interfere with normal organ function. Fibrosis can occur in almost any tissue of the body, including in the lung (pulmonary fibrosis, cystic fibrosis, radiation-induced lung injury), liver (cirrhosis, biliary atresia), heart (arterial fibrosis, endomyocardial fibrosis, prior myocardial infarction), brain, skin (scleroderma, sclerosis), kidney, joints and intestine (Crohn's disease).

Glaucoma: An eye disorder in which the optic nerve suffers damage, permanently damaging vision in the affected eye(s) and progressing to complete blindness if untreated. It is generally associated with increased pressure of the fluid in the eye (aqueous humor).

Hydrogel: A macromolecular polymer gel comprised of a network of crosslinked polymer chains.

Iatrogenic disease or disorder: A disease or disorder caused by medical treatment or a diagnostic procedure. Exemplary iatrogenic diseases/disorders include drug-induced (such as bleomycin-induced) pulmonary fibrosis, Bacillus Calmette-Guerin (BCG) treatment-induced bladder fibrosis, and chemotherapy-induced bladder fibrosis.

Inflammatory disease or disorder: A disease or disorder characterized by inflammation. Examples include, but are not limited to, idiopathic pulmonary fibrosis, allergy, asthma, autoimmune diseases, celiac disease, hepatitis, inflammatory bowel disease, reperfusion injury and transplant rejection.

Macular degeneration: A condition resulting in atrophy or degeneration of the macula. Age-related macular degeneration is a leading cause of visual loss in the elderly. There are two different forms of macular degeneration, referred to as the dry and wet forms. In atrophic macular degeneration (the dry form), there is pigmentary disturbance in the macular region but no elevated macular scar and no hemorrhage or exudation in the region of the macula. In contrast, in exudative macular degeneration (the wet form), there is formation of a subretinal network of choroidal neovascularization.

Matrix metalloproteinase (MMP): A calcium-dependent zinc-containing endopeptidase. MMPs are capable of breaking down components of the extracellular matrix, and are also known to play a role in cleavage of cell-surface receptors, release of apoptotic ligands (such as FAS ligand), and inactivation of chemokines/cytokines.

Neovascular glaucoma: A type of glaucoma that is very difficult to treat. This condition is often caused by proliferative diabetic retinopathy or central retinal vein occlusion. Neovascular glaucoma may also be triggered by other conditions that result in ischemia of the retina or ciliary body. Individuals with poor blood flow to the eye are highly at risk for this condition. Neovascular glaucoma results when new, abnormal vessels begin developing in the angle of the eye that begin blocking the drainage. Patients with this condition begin to rapidly lose their eyesight. Sometimes, the disease appears very rapidly, especially after cataract surgery.

Non-canonical amino acid: An amino acid that is not one of the twenty amino acids encoded directly by triplet codons in the genetic code. Non-canonical amino acids are also referred to as "non-standard" amino acids.

Peptide or polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide," "peptide," or "protein" as used herein are intended to encompass any amino acid sequence and include modified sequences such as glycoproteins. The terms "polypeptide" and "peptide" are specifically intended to cover naturally occurring proteins, as well as those which are recombinantly or synthetically produced. In some embodiments, a peptide is between 10 and 200 amino acids in length, including 10 to 100, 10 to 50, 10 to 30, 15 to 50, 15 to 30 or 18 to 25 amino acids in length. In particular examples, the peptide is about 21 or about 22 amino acids in length. A "residue" refers to an amino acid or amino acid mimetic incorporated in a polypeptide by an amide bond or amide bond mimetic.

Pharmaceutically acceptable carriers: The pharmaceutically acceptable carriers of use are conventional. *Remington's Pharmaceutical Sciences*, by E. W. Martin, Mack Publishing Co., Easton, PA, 15th Edition, 1975, describes compositions and formulations suitable for pharmaceutical delivery of the peptides herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. For topical application to the eye, agents can be mixed, for example, with artificial tears and other emulsions.

Poly(lactic-co-glycolic acid) (PLGA): A biodegradable and biocompatible co-polymer of glycolic acid and lactic acid.

Protease: An enzyme that hydrolyzes (breaks down) proteins and peptides.

Restenosis: The reoccurrence of stenosis, the narrowing of a blood vessel, leading to restricted blood flow. Stenosis (or restenosis) is a form of response to injury leading to wall thickening, narrowing of the lumen, and loss of function in the tissue supplied by the particular passageway. Physical injury during an interventional procedure (such as glaucoma surgery) results in damage to epithelial lining of the tube. The repair of tissues following a physical injury involves regeneration (the replacement of injured cells by cells of the same type) and fibrosis (the replacement of injured cells by connective tissue). The process of fibrosis includes, among other events, the formation of new blood vessels (angiogenesis).

Retinopathy of prematurity: An eye disease that affects prematurely born babies. It is thought to be caused by disorganized growth of retinal blood vessels which may result in scarring and retinal detachment. The disease can be mild and may resolve spontaneously, but it may lead to blindness in serious cases.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a particular polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. In addition, Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least about 75%, for example at least about 80%, 90%, 95%, 96%, 97%, 98% or 99% sequence identity counted over the full length alignment with the amino acid sequence of the polypeptide using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Subject: Living multi-cellular vertebrate organisms, a category that includes both human and veterinary subjects, including human and non-human mammals.

Therapeutically effective amount: A quantity of a specified agent (such as a CXCL peptide) sufficient to achieve a desired effect in a subject, cell or culture being treated with that agent.

III. Overview of Several Embodiments

Activators of the cell surface G-protein coupled receptor CXCR3 can limit and even reverse fibrosis and angiogenesis acting via these receptors on fibroblasts, endothelial cells, pericytes, and other adherent cells. Activation of CXCR3 both stops migration via m-calpain inhibition, and causes anoikis in endothelial cells via μ-calpain cleavage of the β3 integrin. These two actions can be exploited to limit scarring and prevent or reverse angiopathies including those of the eye. The actions of CXCR3 activators are dominant over promoters of fibrosis and angiogenesis.

Cells of the immune response also express the CXCR3 receptor, but respond in a pro-migratory fashion chemotaxing towards these ligands. This creates a potentially confounded situation wherein CXCR3 activators may limit immediate scarring via effects on the adherent cells (such as fibroblasts, endothelial cells, and epithelial cells) while promoting late scarring by attracting and activating immune cells (leukocytes, lymphocytes, macrophages etc.). The actual outcome is determined by the quantitative balance of these two cellular populations. The risk of a late pro-inflammatory reaction is highest in the situation of acute and ongoing inflammation.

To obviate this risk, described herein are activators (ligands) of CXCR3 that can be inactivated by cleavage by extracellular proteases that are present during active inflammation. Inflammatory scarring is accomplished by the production of proteases that degrade the quiescent matrix to replace it with scar matrix. These proteases include a multitude of cathepsins and elastases. Using a ligand for CXCR3 that is sensitive to cleavage by these proteases allows for extinction of the unwanted pro-inflammatory signaling as the ligand is inactivated in the presence of acute inflammation.

The disclosed peptides can be used for the treatment of fibrotic and angiogenic diseases, including for the treatment of scarring, angiopathies, scleroderma and auto-immune fibrosis. These diseases and disorders can occur in any organ of the body, such as in the skin, lung, liver, kidney, heart, and eyes. The diseases also include those caused by wounds, auto-immune pathology, diabetes, and those of unknown etiologies, such as wet age-related macular degeneration (AMD) and idiopathic pulmonary fibrosis (IPF).

Provided herein are recombinant C-X-C motif chemokine ligand (CXCL) peptides that are modified relative to a wild-type CXCL amino acid sequence to introduce a cleavage site for a protease. In some embodiments, the CXCL is a ligand for C-X-C chemokine receptor 3 (CXCR3). In some examples, the CXCL is CXCL10, CXCL4, CXCL9 or CXCL11. In specific non-limiting examples, the CXCL is CXCL10.

In some embodiments, the protease is a protease that is activated during an inflammatory response, such as an acute inflammatory response. In some examples, the protease is a cathepsin, an elastase or a matrix metalloproteinase (MMP). In specific examples, the cathepsin is cathepsin G or cathepsin K. In other specific examples, the MMP is MMP2. In other specific examples, the elastase is a neutrophil elastase.

In some embodiments, the peptide is about 12 to about 30 amino acids in length, such as about 18 to about 25 amino acids in length, such as about 20 to about 23 amino acids in length, such as about 21 or 22 amino acids in length. In some examples, the peptide is 12, 13, 14, 15, 16, 17, 18, 19, 20, 21, 22, 23, 24, 25, 26, 27, 28, 29 or 30 amino acids in length.

In some embodiments, the amino acid sequence of the peptide is at least 90%, at least 91%, at least 92%, at least 93%, at least 94%, at least 95%, at least 96%, at least 97%, at least 98% or at least 99% identical to any one of SEQ ID NOs: 2-7, 17-23 and 27-34. In some examples, the amino acid sequence of the peptide comprises or consists of any one of SEQ ID NOs: 2-7, 17-23 and 27-34.

In some embodiments, the peptide comprises a C-terminal proline that is amidated or methylated.

In some embodiments, the peptide comprises at least one chemical modification. For example, a chemical modification can be introduced in order to inhibit degradation of the peptide and/or increase half-life of the peptide. In some examples, the at least one modification comprises a modification at the N-terminus of the peptide, a modification at the C-terminus of the peptide, or both. In specific non-limiting examples, the modification at the N-terminus comprises formylation, acetylation, propionylation, pyroglutamate formation, myristoylation, palmitylation, S-palmitoylation, mono-methylation, di-methylation, tri-methylation, or any combination thereof. In other specific non-limiting examples, the modification at the C-terminus comprises methylation, alpha-amidation, or a combination thereof. In other embodiments, the at least one modification comprises a non-standard peptide linkage.

In some embodiments, the recombinant CXCL peptide includes at least one D-amino acid. In some examples, the CXCL peptide includes multiple D-amino acids, such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 or at least 21 D-amino acids.

In some embodiments, the recombinant CXCL peptide includes at least one non-canonical amino acid. In some examples, the at least one non-canonical amino acid is a modified non-canonical amino acid. The peptide can include a modified non-canonical amino acid at the N-terminus of the peptide, at the C-terminus of the peptide, or both. In specific non-limiting examples, the peptide includes a modified non-canonical amino acid at the N-terminus and the modification comprises formylation, acetylation, propionylation, pyroglutamate formation, myristoylation, palmitylation, S-palmitoylation, mono-methylation, di-methylation, tri-methylation, or any combination thereof. In other specific non-limiting examples, the peptide comprises a modified non-canonical amino acid at the C-terminus and the modification comprises methylation, alpha-amidation, or a combination thereof.

In some embodiments, the at least one non-canonical amino acid is a methylated amino acid, an amino acid conjugated to a polyethylene glycol polymer, an amino acid conjugated to biotin, an amino acid conjugated to fluorescein isothiocyanate (FITC), an amino acid conjugated to a carrier protein, an amino acid labelled with a radioactive isotope, or any combination thereof. In some examples, the methylated amino acid is a mono-methylated amino acid, di-methylated amino acid, or tri-methylated amino acid. In some examples, the carrier protein is bovine serum albumin, ovalbumin, or keyhole limpet hemocyanin. In some examples, the radioactive isotope is $^{2}H$, $^{15}N$, $^{13}C$, or both $^{15}N$ and $^{13}C$ In some embodiments, the recombinant CXCL peptide is in a slow release formulation. In some examples, the slow release formulation includes poly(lactic-co-glycolic acid) (PLGA), a hydrogel or coacervate.

Also provided herein are compositions that include a recombinant CXCL peptide disclosed herein and a pharmaceutically acceptable carrier. In some embodiments, the composition is formulated for topical, intranasal, inhalation, intravenous, intravitreal, intramuscular, intradermal, or subcutaneous administration. In some examples, the composition is formulated for delivery to the lungs by aerosolization or nebulizer, such as for the treatment of cystic fibrosis. In other examples, the composition is formulated for delivery to the bladder by catheter and instillation. Fibrosis is a major complication of early bladder cancer treatment and chronic bladder infections, leading to irritable bladder syndrome. Thus, a composition formulated for delivery to the bladder could be used to treat these conditions.

In some embodiments, the composition is provided in unit-dose form.

In some embodiments, the composition may include a protease inhibitor, a preservative, a tonicity agent, a buffering agent, a pH adjustment agent, a sterile solvent or any combination thereof. In some embodiments, the protease inhibitor may include, but is not limited to, TIMP1, odanacatib, calpeptin, batimastat, ilomastat, or any combination thereof. In some embodiments, the tonicity agent may include, but is not limited to, an isotonic buffer such as sodium chloride. In some embodiments, the buffering agent may include, but is not limited to, phosphoric acid, acetic acid, citric acid, a phosphate buffer, histidine, tromethamine, gluconic acid, lactic acid, tartaric acid, aspartic acid, glutamic acid, tartaric acid, succinic acid, malic acid, fumaric acid, alpha-ketoglutaric acid, or a combination thereof. In some embodiments, the pH adjustment agent may include, but is not limited to, hydrochloric acid. In some embodiments, the sterile solvent may include, but is not limited to, sterile water. In some embodiments the composition may also include a stabilizer such as, but not limited to trehalose. In some embodiments, the composition may also include a surfactant such as polysorbate.

Further provided herein are methods of inhibiting fibrosis in a subject. In some embodiments, the method includes administering to the subject a CXCL peptide or a composition disclosed herein. In some examples, the subject has a wound, an autoimmune disease, an inflammatory disease or disorder, or an iatrogenic disease or disorder. In specific examples, the autoimmune disease is diabetes, scleroderma or autoimmune fibrosis. In other specific examples, the inflammatory disease or disorder is idiopathic pulmonary fibrosis (IPF). In other specific examples, the iatrogenic disease or disorder is drug-induced (such as bleomycin-induced) pulmonary fibrosis, Bacillus Calmette-Guerin (BCG) treatment-induced bladder fibrosis, or chemotherapy-induced bladder fibrosis.

Also provided herein are methods of inhibiting angiogenesis in a subject. In some embodiments, the method includes administering to the subject a CXCL peptide or a composition disclosed herein. In some examples, the subject has an angiogenic disorder of the eye. In particular examples, the angiogenic disorder of the eye is wet macular degeneration, diabetic retinopathy, retinopathy of prematurity, restenosis following glaucoma treatment, neovascular glaucoma or corneal neovascularization.

IV. Peptide Sequences

The present disclosure describes modified peptides derived from a CXCL protein that functions as a ligand for CXCR3. The disclosed peptides are about 12 to about 30 amino acids in length, such as about 18 to about 25 amino acids in length, such as about 12, about 13, about 14, about 15, about 16, about 17, about 18, about 19, about 20, about 21, about 22, about 23, about 24, about 25, about 26, about 27, about 28, about 29 or about 30 amino acids in length. The peptides are modified to include a protease cleavage site, allowing for inactivation of the peptide in the presence of a protease that recognizes the incorporated cleavage site. In some instances, the cleavage site is a cleavage site for a cathepsin (such as cathepsin G or cathepsin K), an elastase (such as neutrophil elastase), or a MMP (such as MMP2). One of skill in the art is capable of determining appropriate protease cleavage sites, such as with the assistance of online tools, such as ExPASy Bioinformatics Resource Portal or Protease Specificity Prediction Server (PROSPER; see also Song et al., *PLoS One* 7(11):e50300, 2012).

One of skill in the art is capable of identifying and introducing appropriate amino acid substitutions that result in a protease cleavage site. For example, cathepsin G is known to recognize –/V/L/LHF†S/–S/A/V (SEQ ID NO: 12), cathepsin K is known to recognize –/–/LPV/EA†GE/–/–/– (SEQ ID NO: 35), and MMP2 is known to recognize –/P/–/–†LI/–/–/– (SEQ ID NO: 36) (Song et al., *PLoS One* 7(11):e50300, 2012); and neutrophil elastase is known to recognize FIRW (SEQ ID NO: 13) (Schulenburg et al., *Analyst* 141(5):1645-1648, 2016).

In some embodiments, the peptide is derived from human CXCL10, set forth herein as SEQ ID NO: 8. The peptide can be comprised of any portion of CXCL10 that includes about 18 to about 25 consecutive amino acids of SEQ ID NO: 8, wherein one or more amino acids are substituted to introduce a cleavage site for a selected protease, wherein the modified peptide (in the absence of the protease) retains the ability to activate CXCR3.

```
CXCL10 (GENBANK ™ Accession No. NP_001565.3;
SEQ ID NO: 8)
MNQTAILICCLIFLTLSGIQGVPLSRTVRCTSISISNQPVNPRSLEKLEI

IPASQFCPRVEIIATMKKKGEKRCLNPESKAIKNLLKAVSKERSKRSP
```

In some embodiments herein, the CXCL10 peptide is based on the C-terminal peptide:

```
                    (WT; SEQ ID NO: 1)
PESKAIKNLLKAVSKERSKRSP
```

SEQ ID NO: 1 can be modified to introduce a protease cleavage site, such as a cathepsin neutrophil cathepsin or neutrophil elastase cleavage site. Non-limiting examples of modified peptides based on human CXCL10 are provided below.

Exemplary peptides with a cathepsin G and neutrophil elastase cleavage site sequence:

```
(Peptide 110; SEQ ID NO: 2)
PESKAIKNLLKAVHKEMSKRSP

(Peptide 112; SEQ ID NO: 3)
_ESKAIKNLLKAVHKEMSKRSP

(Peptide 116; SEQ ID NO: 4)
PESKAIKNLLKAVHKERSKRSP

(Peptide 117; SEQ ID NO: 5)
_ESKAIKNLLKAVHKERSKRSP
```

Peptide with a neutrophil cathepsin cleavage site:

```
(Peptide 121; SEQ ID NO: 6)
PESKAIKNLLKAVSEVLSKRSP
```

Peptide with a neutrophil elastase cleavage site:

```
(Peptide 131; SEQ ID NO: 7)
PESFIRWNLLKAVSKEMSKRSP
```

For the peptides of SEQ ID NOs: 2, 3 and 7, the arginine (R) to methionine (M) substitution is unrelated to the mutation(s) that introduce a protease cleavage site.

In some embodiments, the peptide is derived from human CXCL4, set forth herein as SEQ ID NO: 9. The peptide can be comprised of any portion of CXCL4 that includes about 18 to about 25 consecutive amino acids of SEQ ID NO: 9, wherein one or more amino acids are substituted to introduce a cleavage site for a selected protease, wherein the modified peptide (in the absence of the protease) retains the ability to activate CXCR3.

```
CXCL4 (GENBANK ™ Accession No. NP_002610.1;
SEQ ID NO: 9)
MSSAAGFCASRPGLLFLGLLLLPLVVAFASAEAEEDGDLQCLCVKTTSQ

VRPRHITSLEVIKAGPHCPTAQLIATLKNGRKICLDLQAPLYKKIIKKL

LES
```

In some embodiments, the modified CXCL4 peptide is based on one of the following CXCL4 peptides:

```
(SEQ ID NO: 14)
DLQCLCVKTTSQVRPRHITSLEVIKAGPH

(SEQ ID NO: 15)
PLYKKIIKKLLES

(SEQ ID NO: 16)
LDLQAPLYKKIIKKLLES
```

SEQ ID NO: 14, 15 or 16 can be modified to introduce a protease cleavage site, such as a cathepsin K or matrix metalloproteinase 2 (MMP2) cleavage site. Non-limiting examples of modified peptides based on human CXCL4 are provided below.

Exemplary peptides with a cathepsin K cleavage site sequence:

```
(SEQ ID NO: 17)
DLQCLCVKTTSQVRPRHITSLEGIKAGPH
```

-continued

```
(SEQ ID NO: 18)
DLQCLCVKTTSQVRPRHITSLEEIKAGPH

(SEQ ID NO: 19)
PLYKKIIKKLEES

(SEQ ID NO: 20)
LDLQAPLYKKIIKKLEES
```

Exemplary peptides with a MMP2 cleavage site sequence:

```
(SEQ ID NO: 21)
DLQCLCVKTTSQVRPRLITSLEVIKAGPH

(SEQ ID NO: 22)
PLYPKIIKKLLES

(SEQ ID NO: 23)
LDLQAPLYPKIIKKLLES
```

In some embodiments, the peptide is derived from human CXCL9, set forth herein as SEQ ID NO: 10. The peptide can be comprised of any portion of CXCL9 that includes about 18 to about 25 consecutive amino acids of SEQ ID NO: 10, wherein one or more amino acids are substituted to introduce a cleavage site for a selected protease, wherein the modified peptide (in the absence of the protease) retains the ability to activate CXCR3.

```
CXCL9 (GENBANK ™ Accession No. NP_002407.1;
SEQ ID NO: 10)
MKKSGVLFLLGIILLVLIGVQGTPVVRKGRCSCISTNQGTIHLQSLKDLK

QFAPSPSCEKIEIIATLKNGVQTCLNPDSADVKELIKKWEKQVSQKKKQK

NGKKHQKKKVLKVRKSQRSRQKKTT
```

In some embodiments, the peptide is derived from human CXCL11, set forth herein as SEQ ID NO: 11. The peptide can be comprised of any portion of CXCL11 that includes about 18 to about 25 consecutive amino acids of SEQ ID NO: 11, wherein one or more amino acids are substituted to introduce a cleavage site for a selected protease, wherein the modified peptide (in the absence of the protease) retains the ability to activate CXCR3.

```
CXCL11 (GENBANK ™ Accession No. NP_005400.1;
SEQ ID NO: 11)
MSVKGMAIALAVILCATVVQGFPMFKRGRCLCIGPGVKAVKVADIEKASI

MYPSNNCDKIEVIITLKENKGQRCLNPKSKQARLIIKKVERKNF
```

In some embodiments, the modified CXCL11 peptide is based on one of the following CXCL11 peptides:

```
(SEQ ID NO: 24)
PKSKQARLIIKKVERKNF

(SEQ ID NO: 25)
LNPKSKQARLIIKKVERKNF

(SEQ ID NO: 26)
DKIEVIITLKENKGQR
```

SEQ ID NO: 24, 25 or 26 can be modified to introduce a protease cleavage site, such as a cathepsin K or MMP2 cleavage site. Non-limiting examples of modified peptides based on human CXCL11 are provided below.

Exemplary peptides with a cathepsin K cleavage site sequence:

(SEQ ID NO: 27)
PKSKQARLIIKKVEEKNF (SEQ ID NO: 28)
PKSKQARLIIKKVEGKNF (SEQ ID NO: 29)
LNPKSKQARLIIKKVEEKNF (SEQ ID NO: 30)
LNPKSKQARLIIKKVEGKNF (SEQ ID NO: 31)
DKIEVIITLEENKGQR

Exemplary peptides with a MMP2 cleavage site sequence:

(SEQ ID NO: 32)
PKSKPARLIIKKVERKNF (SEQ ID NO: 33)
LNPKSKPARLIIKKVERKNF (SEQ ID NO: 34)
DKPEVIITLKENKGQR

V. Exemplary Embodiments

1. A recombinant C-X-C motif chemokine ligand (CXCL) peptide, wherein the peptide is modified relative to a wild-type CXCL amino acid sequence to introduce a cleavage site for a protease.

2. The recombinant CXCL peptide of embodiment 1, wherein the CXCL is a ligand for C-X-C chemokine receptor 3 (CXCR3).

3. The recombinant CXCL peptide of embodiment 1 or embodiment 2, wherein the CXCL is CXCL10, CXCL4, CXCL9 or CXCL11.

4. The recombinant CXCL peptide of any one of embodiments 1-3, wherein the protease is a cathepsin, an elastase or a matrix metalloproteinase (MMP).

5. The recombinant CXCL peptide of embodiment 4, wherein the cathepsin is cathepsin G.

6. The recombinant CXCL peptide of embodiment 4, wherein the cathepsin is cathepsin K.

7. The recombinant CXCL peptide of embodiment 4, wherein the elastase is a neutrophil elastase.

8. The recombinant CXCL peptide of embodiment 4, wherein the MMP is MMP2.

9. The recombinant CXCL peptide of any one of embodiments 1-8, wherein the peptide is about 12 to about 30 amino acids in length.

10. The recombinant CXCL peptide of any one of embodiments 1-9, wherein the peptide is about 18 to about 25 amino acids in length.

11. The recombinant CXCL peptide of any one of embodiments 1-10, wherein the peptide is 21 or 22 amino acids in length.

12. The recombinant CXCL peptide of any one of embodiments 1-11, wherein the amino acid sequence of the peptide is at least 90% identical to any one of SEQ ID NOs: 2-7.

13. The recombinant CXCL peptide of any one of embodiments 1-11, wherein the amino acid sequence of the peptide is at least 95% identical to any one of SEQ ID NOs: 2-7.

14. The recombinant CXCL peptide of any one of embodiments 1-11, wherein the amino acid sequence of the peptide comprises or consists of any one of SEQ ID NOs: 2-7.

15. The recombinant CXCL peptide of any one of embodiments 1-14, wherein the amino acid sequence of the peptide comprises or consists of SEQ ID NO: 2.

16. The recombinant CXCL peptide of any one of embodiments 1-15, wherein the peptide comprises at least one modification.

17. The recombinant CXCL peptide of embodiment 16, wherein the at least one modification comprises a modification at the N-terminus of the peptide, a modification at the C-terminus of the peptide, or both.

18. The recombinant CXCL peptide of embodiment 17, wherein the modification at the N-terminus comprises formylation, acetylation, propionylation, pyroglutamate formation, myristoylation, palmitylation, S-palmitoylation, mono-methylation, di-methylation, tri-methylation, or any combination thereof.

19. The recombinant CXCL peptide of embodiment 17 or embodiment 18, wherein the modification at the C-terminus comprises methylation, alpha-amidation, or a combination thereof.

20. The recombinant CXCL peptide of embodiment 16, wherein the at least one modification comprises a non-standard peptide linkage.

21. The recombinant CXCL peptide of any one of embodiments 1-20, comprising at least one D-amino acid.

22. The recombinant CXCL peptide of any one of embodiments 1-21, comprising at least one non-canonical amino acid.

23. The recombinant CXCL peptide of embodiment 22, wherein the at least one non-canonical amino acid is a modified non-canonical amino acid.

24. The recombinant CXCL peptide of embodiment 23, wherein the peptide comprises a modified non-canonical amino acid at the N-terminus of the peptide, at the C-terminus of the peptide, or both.

25. The recombinant CXCL peptide of embodiment 24, wherein the peptide comprises a modified non-canonical amino acid at the N-terminus and the modification comprises formylation, acetylation, propionylation, pyroglutamate formation, myristoylation, palmitylation, S-palmitoylation, mono-methylation, di-methylation, tri-methylation, or any combination thereof.

26. The recombinant CXCL peptide of embodiment 24 or embodiment 25, wherein the peptide comprises a modified non-canonical amino acid at the C-terminus and the modification comprises methylation, alpha-amidation, or a combination thereof.

27. The recombinant CXCL peptide of embodiment 22, wherein the at least one non-canonical amino acid is a methylated amino acid, an amino acid conjugated to a polyethylene glycol polymer, an amino acid conjugated to biotin, an amino acid conjugated to fluorescein isothiocyanate (FITC), an amino acid conjugated to a carrier protein, an amino acid labelled with a radioactive isotope, or any combination thereof.

28. The recombinant CXCL peptide of any one of embodiments 1-27 in a slow release formulation.

29. The recombinant CXCL peptide of embodiment 28, wherein the slow release formulation comprises poly(lactic-co-glycolic acid) (PLGA), a hydrogel or coacervate.

30. A composition comprising the recombinant CXCL peptide of any one of embodiments 1-29 and a pharmaceutically acceptable carrier.

31. The composition of embodiment 30, formulated for topical, intranasal, inhalation, intravenous, intravitreal, intramuscular, intradermal, or subcutaneous administration.

32. The composition of embodiment 30, formulated for delivery to the lungs by aerosolization or nebulizer.

33. The composition of embodiment 30, formulated for delivery to the bladder by catheter and instillation.

34. The composition of any one of embodiments 30-33 in unit-dose form.

35. A method of inhibiting fibrosis in a subject, comprising administering to the subject the CXCL peptide of any one of embodiments 1-29 or the composition of any one of embodiments 30-34.

36. The method of embodiment 35, wherein the subject has a wound, an autoimmune disease, an inflammatory disease or disorder, or an iatrogenic disease or disorder.

37. The method of embodiment 36, wherein the autoimmune disease is diabetes, scleroderma or autoimmune fibrosis.

38. The method of embodiment 36, wherein the inflammatory disease or disorder is idiopathic pulmonary fibrosis (IPF).

39. The method of embodiment 36, wherein the iatrogenic disease or disorder is drug-induced pulmonary fibrosis, Bacillus Calmette-Guerin (BCG) treatment-induced bladder fibrosis, or chemotherapy-induced bladder fibrosis.

40. A method of inhibiting angiogenesis in a subject, comprising administering to the subject the CXCL peptide of any one of embodiments 1-29 or the composition of any one of embodiments 30-34.

41. The method of embodiment 40, wherein the subject has an angiogenic disorder of the eye.

42. The method of embodiment 41, wherein the angiogenic disorder of the eye is wet macular degeneration, diabetic retinopathy, retinopathy of prematurity, restenosis following glaucoma treatment, neovascular glaucoma or corneal neovascularization.

The following examples are provided to illustrate certain particular features and/or embodiments. These examples should not be construed to limit the disclosure to the particular features or embodiments described.

EXAMPLES

Example 1

Modified Peptides Susceptible to Protease Cleavage

This example describes a peptide engineered to be susceptible to cleavage by extracellular proteases of the acute inflammatory response.

Previous studies demonstrated that linear peptide fragments of the natural ligands for CXCR3 (such as CXCL10) are capable of binding to and activating CXCR3 (see U.S. Pat. Nos. 9,180,167; 9,452,200; and 9,872,889, the contents of which are herein incorporated by reference in their entirety). Chemokines that signal through CXCR3 can both induce anti-fibrotic effects on adherent cells and promote inflammatory and fibrotic effects on cells of the innate immune system. To limit the fibrotic effects of CXCR3 activators during an inflammatory response, a peptide susceptible to cleavage by proteases present during an acute inflammatory response was designed. Thus, upon induction of an inflammatory response, the engineered peptide is cleaved, thereby limiting its pro-fibrotic effects.

Peptide 110 (SEQ ID NO: 2) is a modified fragment of human CXCL10 (also known as IP-10). Compared to the wild-type human sequence (SEQ ID NO: 1), Peptide 110 contains an arginine to methionine substitution and replaces a serine residue with a histidine. The latter substitution results in the introduction of a cathepsin G and neutrophil elastase cleavage site. The substituted residues are indicated in bold underline:

```
Human sequence:
                                     (SEQ ID NO: 1)
PESKAIKNLLKAVSKERSKRSP

Peptide 110:
                                     (SEQ ID NO: 2)
PESKAIKNLLKAVHKEMSKRSP
```

Since the histidine to serine substitution is a non-conserved amino acid change, experiments were performed to confirm that the engineered peptide retained the ability to block angiogenesis and fibrosis in a mouse model of choroidal neovascularization (CNV).

Laser-Induced CNV

Mouse CNV was induced by laser photocoagulation-induced rupture of Bruch's membrane as previously described. Briefly, 7- to 8-week-old female C57BL/6J mice were anesthetized with ketamine hydrochloride (100 mg/kg body weight), and pupils were dilated with 1% tropicamide. Three burns of 532-nm diode laser photocoagulation (spot size, 75 mm; duration, 0.1 sec; power, 120 mW) were delivered to each retina with the slit lamp delivery system of an OcuLight GL diode laser (Iridex, Mountain View, CA), using a coverslip as a contact lens to view the retina. Burns were performed at the 9, 12, and 3 o'clock positions of the posterior pole of the retina. Production of a bubble at the time of lasering, which indicates rupture of Bruch's membrane, is an important factor in obtaining choroidal neovascularization (NV), and therefore only burns in which a bubble was produced were included in the study.

Immediately after laser treatment, mice were injected with either 1 μg (FIG. 1A) or 3 μg (FIG. 1B) of Peptide 110 (SEQ ID NO: 2), or one of three positive control peptides (Peptide 102, Peptide 105 or Peptide 107), in a volume of 1 μl in one eye and the contralateral eyes were injected with scramble peptide as control. Other control mice were injected with vehicle only. After injection, the corneas were protected with antibiotic ointment. Seven days after laser treatment, the mice were euthanized. The eyes were enucleated and fixed in 10% PBS-buffered Formalin for 3 hours. Choroids were dissected and put in 1.5 ml Eppendorf tubes and stained with FITC conjugated GSA-Lectin IB4 (1:150, Vector, Frederick, MD) at 4° C. with rotation overnight. After three washes with PBST, choroids were mounted on glass slides and were examined by fluorescence microscopy. Images were digitized with a three-color CCD video camera and a frame grabber. Image analysis software (Image-Pro Plus; MediaCybernetics, Silver Spring, MD) was used to measure the total area of choroidal NV at each rupture site.

Figure 1B:
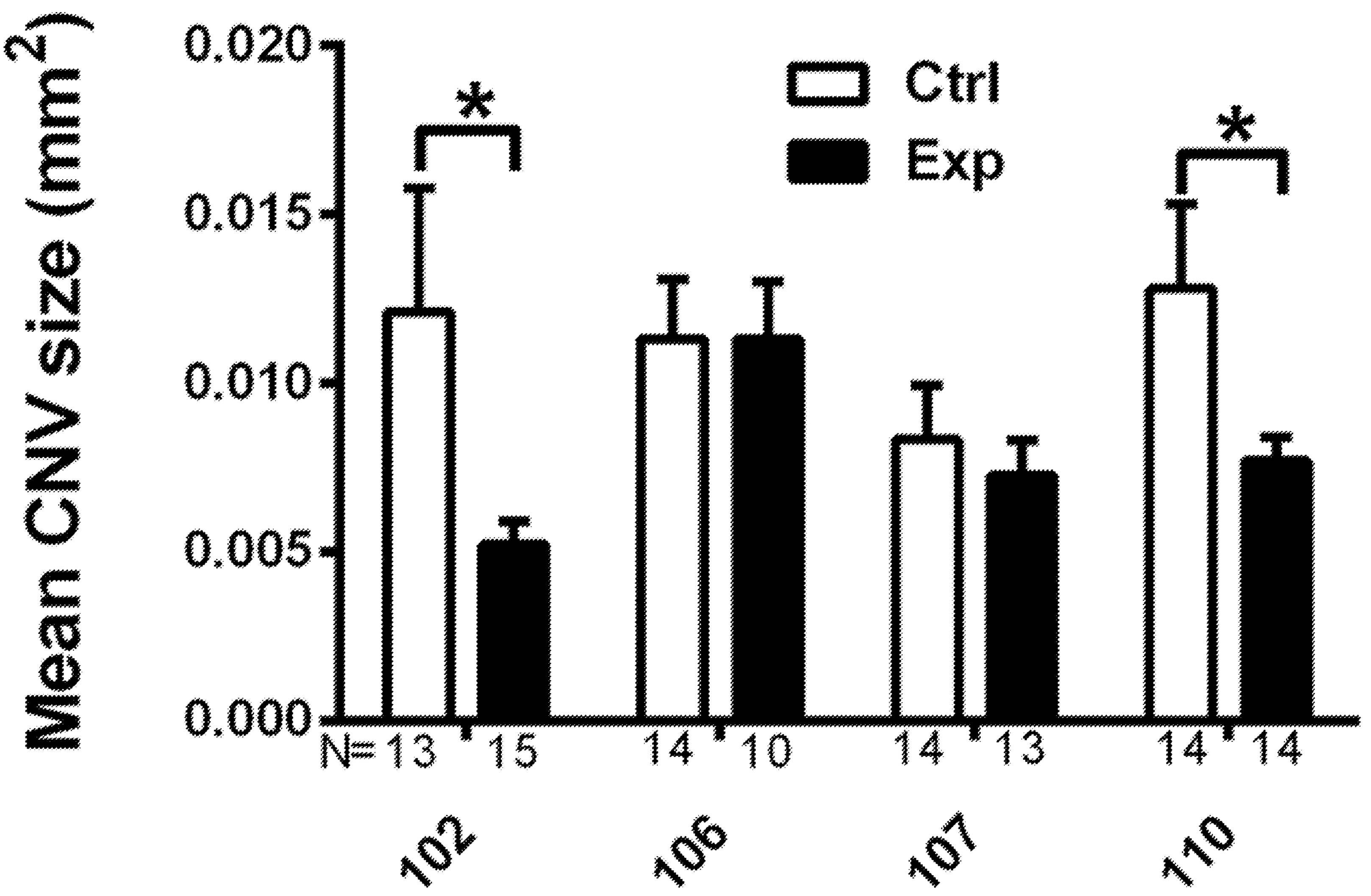

As shown in FIGS. 1A-1B, Peptide 110 retained its anti-angiogenic activity as evidenced by a significant reduction in choroidal neovascularization at both doses of peptide.

Example 2

CXCR3 Activating Peptides with an Engineered Protease Cleavage Site

This example describes additional peptides based on the sequence of human CXCL10, human CXCL4 or human CXCL11 designed to contain one or more cleavage sites for proteases activated during acute inflammation.

CXCL10-derived peptides with a cathepsin G and neutrophil elastase cleavage site:

(Peptide 110; SEQ ID NO: 2)
PESKAIKNLLKAVHKEMSKRSP (Peptide 112; SEQ ID NO: 3)
_ESKAIKNLLKAVHKEMSKRSP (Peptide 116; SEQ ID NO: 4)
PESKAIKNLLKAVHKERSKRSP (Peptide 117; SEQ ID NO: 5)
_ESKAIKNLLKAVHKERSKRSP CXCL10-derived peptide with a neutrophil cathepsin cleavage site:

(Peptide 121; SEQ ID NO: 6)
PESKAIKNLLKAVSEVLSKRSP

CXCL10-derived peptide with a neutrophil elastase cleavage site:

(Peptide 131; SEQ ID NO: 7)
PESFIRWNLLKAVSKEMSKRSP

CXCL4-derived peptides with a cathepsin K cleavage site sequence:

(SEQ ID NO: 17)
DLQCLCVKTTSQVRPRHITSLEGIKAGPH (SEQ ID NO: 18)
DLQCLCVKTTSQVRPRHITSLEEIKAGPH (SEQ ID NO: 19)
PLYKKIIKKLEES (SEQ ID NO: 20)
LDLQAPLYKKIIKKLEES

CXCL4-derived peptides with a MMP2 cleavage site sequence:

(SEQ ID NO: 21)
DLQCLCVKTTSQVRPRLITSLEVIKAGPH (SEQ ID NO: 22)
PLYPKIIKKLLES (SEQ ID NO: 23)
LDLQAPLYPKIIKKLLES

CXCL11-derived peptides with a cathepsin K cleavage site sequence:

(SEQ ID NO: 27)
PKSKQARLIIKKVEEKNF (SEQ ID NO: 28)
PKSKQARLIIKKVEGKNF (SEQ ID NO: 29)
LNPKSKQARLIIKKVEEKNF (SEQ ID NO: 30)
LNPKSKQARLIIKKVEGKNF (SEQ ID NO: 31)
DKIEVIITLEENKGQR

CXCL11-derived peptides with a MMP2 cleavage site sequence:

(SEQ ID NO: 32)
PKSKPARLIIKKVERKNF (SEQ ID NO: 33)
LNPKSKPARLIIKKVERKNF (SEQ ID NO: 34)
DKPEVIITLKENKGQR

In view of the many possible embodiments to which the principles of the disclosed subject matter may be applied, it should be recognized that the illustrated embodiments are only preferred examples of the disclosure and should not be taken as limiting the scope of the disclosure. Rather, the scope of the disclosure is defined by the following claims. We therefore claim as our invention all that comes within the scope and spirit of these claims.

The invention claimed is:

1. A recombinant C-X-C motif chemokine ligand (CXCL) peptide, comprising a modification relative to a wild-type CXCL amino acid sequence, wherein the modification is a cleavage site for a protease and wherein the amino acid sequence of the peptide comprises SEQ ID NO: 2.

2. The recombinant CXCL peptide of claim 1, wherein the protease is cathepsin G or neutrophil elastase.

3. The recombinant CXCL peptide of claim 1, wherein the peptide further comprises at least one chemical modification.

4. The recombinant CXCL peptide of claim 3, wherein the at least one chemical modification comprises a modification at the N-terminus of the peptide, a modification at the C-terminus of the peptide, or both.

5. The recombinant CXCL peptide of claim 4, wherein the modification at the N-terminus comprises formylation, acetylation, propionylation, pyroglutamate formation, myristoylation, palmitylation, S-palmitoylation, mono-methylation, di-methylation, tri-methylation, or any combination thereof.

6. The recombinant CXCL peptide of claim 4, wherein the modification at the C-terminus comprises methylation, alpha-amidation, or a combination thereof.

7. The recombinant CXCL peptide of claim 1 in a slow release formulation.

8. A composition comprising the recombinant CXCL peptide of claim 1 and a pharmaceutically acceptable carrier.

9. A recombinant C-X-C motif chemokine ligand (CXCL) peptide, comprising a modification relative to a wild-type CXCL amino acid sequence, wherein the modification is a cleavage site for a protease, and wherein the amino acid sequence of the peptide consists of SEQ ID NO: 2.

* * * * *